United States Patent
Kloke et al.

(10) Patent No.: US 12,201,982 B2
(45) Date of Patent: Jan. 21, 2025

(54) 3D SCAFFOLD COMPRISING A BIOCOMPATIBLE POLYMER WITH A COLONIZATION CHAMBER OPEN AT THE TOP FOR BIOLOGICAL CELLS, AND WITH A CANAL VESSEL SURROUNDING THE COLONIZATION CHAMBER

(71) Applicant: CELLBRICKS GmbH, Berlin (DE)

(72) Inventors: Lutz Kloke, Berlin (DE); Alexander Thomas, Berlin (DE)

(73) Assignee: CELLBRICKS GmbH, Berlin (DE)

( * ) Notice: Subject to any disclaimer, the term of this patent is extended or adjusted under 35 U.S.C. 154(b) by 0 days.

(21) Appl. No.: 17/779,991

(22) PCT Filed: Nov. 20, 2020

(86) PCT No.: PCT/DE2020/100984
§ 371 (c)(1),
(2) Date: Nov. 19, 2022

(87) PCT Pub. No.: WO2021/104570
PCT Pub. Date: Jun. 3, 2021

(65) Prior Publication Data
US 2023/0158501 A1   May 25, 2023

(30) Foreign Application Priority Data

Nov. 27, 2019   (DE) .......................... 10 2019 132 211

(51) Int. Cl.
*B33Y 80/00*   (2015.01)
*B01L 3/00*   (2006.01)
(Continued)

(52) U.S. Cl.
CPC ... *B01L 3/502761* (2013.01); *B01L 3/502707* (2013.01); *B33Y 70/00* (2014.12);
(Continued)

(58) Field of Classification Search
None
See application file for complete search history.

(56) References Cited

U.S. PATENT DOCUMENTS

2003/0175410 A1   9/2003   Campbell
2021/0107212 A1   4/2021   Kloke

FOREIGN PATENT DOCUMENTS

EP   3018531 A1   5/2016
JP   2017536113 A   12/2017
(Continued)

OTHER PUBLICATIONS

Ugolini et al., Adv. Healthcare Mater. 2017, 6, 1601170, 7 pages (Year: 2017).*

(Continued)

*Primary Examiner* — Evelyn Y Pyla
(74) *Attorney, Agent, or Firm* — Calvert Technology Law, PLLC; Nathan H. Calvert

(57) ABSTRACT

A 3D scaffold (3-dimensional scaffold) is comprised of a biocompatible polymer. The 3D scaffold includes a recess that is open towards the top side of the 3D scaffold as a colonization chamber for biological cells, a canal-type vessel, which at least partially surrounds the colonization chamber, a filling opening for the canal-type vessel, and an outlet opening for the canal-type vessel. A production method for the 3D scaffold is also provided and the 3D scaffold is used for colonizing the colonization chamber with biological cells.

14 Claims, 2 Drawing Sheets

(51) Int. Cl.
*B33Y 70/00* (2020.01)
*C12M 1/00* (2006.01)
*C12M 1/32* (2006.01)
*C12M 3/06* (2006.01)

(52) U.S. Cl.
CPC ............. *B33Y 80/00* (2014.12); *C12M 23/12* (2013.01); *C12M 23/16* (2013.01); *C12M 23/20* (2013.01)

(56) References Cited

FOREIGN PATENT DOCUMENTS

| WO | 2009042671 | A1 | | 4/2009 | |
|---|---|---|---|---|---|
| WO | 2009048435 | A1 | | 4/2009 | |
| WO | 2011038373 | A2 | | 3/2011 | |
| WO | WO-2018162764 | A1 | * | 9/2018 | ............... A61F 2/28 |
| WO | 2019219605 | A1 | | 11/2019 | |

OTHER PUBLICATIONS

International Search Report and Written Opinion issued Mar. 3, 2021 in PCT/DE2020/100984.
Zhang Rujing: "Stereolithographic hydrogel printing of 3D microfluidic cell culture chips—PhD Thesis", DTU Nanotech, Oct. 1, 2017 (Oct. 1, 2017), XP055775960, URL:http://orbit.dtu.dk/files/142686115/Untitled.pdf.
Zhang Rujing et al: "Stereolithographic hydrogel printing of 3D culture chips with biofunctionalized complex 3D perfusion networks", Lab on a Chip, vol. 17, No. 24, Jan. 1, 2017 (Jan. 1, 2017), pp. 4273-4282, XP055775953.
Xia C, Fang NX. 3D microfabricated bioreactor with capillaries. Biomed Microdevices. Dec. 2009.
Kuo AP, Bhattacharjee N, Lee YS, Castro K, Kim YT, Folch A., High-Precision Stereolithography of Biomicrofluidic Devices. Adv Mater Technol. 2019.
Grix T, Ruppelt A, Thomas A, Amler AK, Noichl BP, Lauster R, Kloke L., Bioprinting Perfusion-Enabled Liver Equivalents for Advanced Organ-on-a-Chip Applications. Genes (Basel). Mar. 22, 2018;9(4):176.
Thomas Alexander et al: "Vascular bioprinting with enzymatically degradable bioinks via multi-material projection-based stereolithography", Acta Biomaterialia, vol. 117, Sep. 24, 2020 (Sep. 24, 2020), pp. 121-132, XP086330240.
International Search Report and Written Opinion issued Mar. 3, 2021 in PCT/DE2020/100986.
German Office Action dated Oct. 8, 2020, in German patent application No. 102019132214.6.
Haemobrick Seeding Protocol, Cellbricks GmbH, Jun. 29, 2020.
Japanese Office action dated Nov. 15, 2022, in Japanese patent application No. 2022-530944.
Japanese Office action dated Apr. 12, 2023, in Japanese patent application No. 2022-530944.
German Patent Office action issued Jul. 10, 2020 in German Patent Application 10 2019 132 211.1.

* cited by examiner

3D SCAFFOLD COMPRISING A BIOCOMPATIBLE POLYMER WITH A COLONIZATION CHAMBER OPEN AT THE TOP FOR BIOLOGICAL CELLS, AND WITH A CANAL VESSEL SURROUNDING THE COLONIZATION CHAMBER

TECHNICAL FIELD OF THE INVENTION

The present invention relates to a 3D scaffold (3-dimensional scaffold) consisting of a biocompatible polymer, which scaffold has the following: a recess that is open towards the top side of the 3D scaffold as a colonization chamber for biological cells, a canal-type vessel, which at least partially surrounds the colonization chamber, in the interior of the 3D scaffold, a filling opening for the canal-type vessel and an outlet opening for the canal-type vessel. The present invention furthermore relates to the production of the 3D scaffold according to the invention, and the use thereof for colonizing the colonization chamber with biological cells.

BACKGROUND OF THE INVENTION

Currently, there are only a few possibilities for producing 3D cell cultures which can be perfused with a nutrient solution, such as e.g. blood. The only possibilities to date are to combine spheroids and microfluidic platforms in order to simulate a directed flow of a nutrient solution. In contrast, by means of a 3D scaffold according to the invention it is possible for the first time to culture biological cells in special three-dimensional architectures which can be supplied with a nutrient solution via a vessel.

Spheroids are tightly packed groups of cells with a round shape. They lack any physiological shape. Moreover, should a user wish to work with several cell types in parallel in one object, their only option is to form a spheroid from the desired cell types. However, in this case the shape of the spheroid is undirected and leads to a random distribution of the cells in the spheroid. This process does not make it possible, therefore, to position the cells discretely from one another. A vessel system cannot be constructed in a targeted manner through casting or spheroids. The only possibility is a spontaneous self-organization by cells, which, however, is uncontrolled and cannot be reproduced. A connection to a microfluidic platform is also not possible, as the respective connections are in each case positioned at a defined location.

The previous possibilities only allow these abovementioned conditions to be reproduced insufficiently, or not at all. In contrast, a 3D scaffold according to the invention offers a possibility of creating complex biological cell architectures which can be supplied with nutrients via a vessel and connected to a microfluidic platform. A 3D scaffold presented here is intended in particular for a user who does not have access to lithographic 3D printing or bioprinting, but would like to produce 3D cell culture constructs.

EP 3 018 531 A1 describes a 3D printing method which makes it possible to work with multiple bio-inks or cell types in parallel in a printing process. The 3D cell culture constructs here are already constructed in parallel with the production of a matrix comprising a biocompatible polymer. However, this method is not suitable for users who themselves do not have a lithographic 3D printing device available.

SUMMARY OF THE INVENTION

Therefore, the object of the present invention is to provide a way in which a 3D cell culture construct can be produced in a simple manner, with a high degree of reproducibility and a high degree of similarity with the physiological architecture, and can be supplied with a nutrient solution via a canal-type vessel and connected to a microfluidic platform.

1 The object according to the invention is achieved by a 3D scaffold comprising a biocompatible polymer. A 3D scaffold in accordance with the present invention has a recess that is open towards the top side of the 3D scaffold as a colonization chamber for biological cells, a canal-type vessel, which at least partially surrounds the colonization chamber, in the interior of the 3D scaffold, a filling opening for the canal-type vessel, and an outlet opening for the canal-type vessel.

The canal-type vessel, which may be referred to herein and in the following claims as a "canal vessel," ensures that every part of the cell culture in the colonization chamber of the 3D scaffold is supplied with sufficient oxygen and nutrients. This is because a tissue which cannot receive a sufficient supply, due to lack of vascularization, risks dying or losing its function. As described in more detail further below, the 3D scaffold according to the invention is produced by lithographic 3D printing. This makes it possible for the first time to construct a vessel system in a targeted manner. Moreover, the 3D scaffold can be printed reproducibly such that it is in each case compatible with the previously selected microfluidic system.

By a biocompatible polymer it is meant a biological or biologically compatible polymer, wherein a biological polymer (polymer occurring in living organisms) is preferred. "Biologically compatible" as used herein means that it does not influence the lifespan of the biological cells, particularly therefore does not have a toxic effect on the biological cells.

The expression "comprising a biocompatible polymer" as used herein means that the 3D scaffold is preferably constructed using a matrix of one or more biocompatible polymers. Although this does not rule out the 3D scaffold containing other constituents aside from biocompatible polymers, it is also possible that the 3D scaffold only consists of biocompatible polymer.

The top side of the 3D scaffold preferably lies in the horizontal plane which is spanned by the X and Y axes. Likewise, the underside preferably also lies in the horizontal plane which is also spanned by the X and Y axes. The top side and underside are preferably substantially congruent. The height or depth of the 3D scaffold extends in the direction of the Z axis.

In some designs of a 3D scaffold according to the invention, it is preferred that the colonization chamber and the canal-type vessel are spatially separated from each other by a separation region comprising a biocompatible polymer, wherein the biocompatible polymer of the separation region is designed such that nutrients diffuse out of a liquid in the canal-type vessel into the colonization chamber.

In some designs of a 3D scaffold according to the invention, it is preferred that the recess that is open towards the top side is arranged in the middle of the top side with respect to the horizontal plane which is spanned by the X and Y axes and extends in a direction perpendicular to the horizontal plane, the Z axis, towards the underside of the 3D scaffold. In the direction of the underside the recess is capped off by biocompatible polymer, with the result that a cell suspension with which the recess has been filled cannot escape. At the side of the plane which is spanned by the X and Y axes, the recess in these designs is surrounded by an edge of the 3D scaffold. The dimensions of this edge of the 3D scaffold are preferably formed such that the filling opening for the canal-type vessel is also arranged on the top side of the 3D scaffold.

The recess that is open towards the top side is preferably formed annular, circular, oval or in a mixed form thereof with respect to its horizontal extent. The recess that is open towards the top side is preferably formed mirror-symmetrical with respect to its horizontal extent. In the plane which is spanned by the X and Y axes, the size of the extent of the recess preferably decreases in the direction of the Z axis towards the underside, preferably in steps. The recess may have a first and a second plane which are both spanned by the X and Y axes. In these designs size of the extent of the first plane is greater than the size of the extent of the second plane (both with respect to their extent in planes which are spanned by the X and Y axes), and may merge into each other with a step.

The first plane preferably lies closer to the top side of the 3D scaffold than the second plane. Above the second plane the recess chamber is preferably surrounded by the canal-type vessel, which preferably extends substantially along a plane which is spanned by the X and Y axes ("substantially" is to mean herein that the canal-type vessel can have a slight downward slope in relation to the direction of the Z axis). Due to the spatial proximity of the recess chamber above the second plane, the recess can be supplied with nutrients from the canal-type vessel.

It is furthermore preferred that the canal-type vessel runs below the first plane, with the result that the recess chamber is also spatially adjacent above the first plane and can be supplied with nutrients from the canal-type vessel.

In further designs of the 3D scaffold according to the invention, it is preferred that the canal-type vessel annularly surrounds the recess that is open towards the top side.

A 3D scaffold according to the invention preferably has two filling openings for the canal-type vessel, which are preferably arranged on the top side of the 3D scaffold. The two filling openings are preferably arranged on opposite sides. This has the advantage that a canal-type vessel running annularly around the recess can be evenly supplied with a nutrient solution.

A 3D scaffold according to the invention preferably has two outlet openings for the canal-type vessel, which are preferably arranged on the lateral surfaces of the 3D scaffold which run perpendicular to the plane of the top side. The two outlet openings are preferably arranged on opposite sides of the 3D scaffold. The presence of two filling openings and two outlet openings of a canal-type vessel that is formed annular makes it possible to supply the biological cells evenly with nutrients.

A 3D scaffold according to the invention is obtainable by a lithographic 3D printing method. This method is described in more detail further below.

The present invention also relates to 3D scaffolds according to the invention, in which the colonization chamber is colonized with biological cells. Biological cells, which are cultured as a 3D cell culture construct, are preferably located in the colonization chamber. In this case, the canal-type vessel can either be colonized with biological cells or not. The canal-type vessel may, however, also be colonized with cells, such as endothelial cells to form the wall of a blood vessel. In this case, the endothelial cells may colonize the inner surface of the canal-type vessel. The colonization with biological cells in the colonization chamber or in the canal-type vessel is preferably effected by filling the colonization chamber or the canal-type vessel with a liquid. In the latter case preferably via the filling opening(s) in some implementations.

The liquid used for colonizing the colonization chamber or the canal-type vessel is preferably a suspension containing biological cells (called cell suspension in the following). In further embodiments, the liquid used for colonizing the colonization chamber preferably contains cell spheroids. In further embodiments, the liquid used preferably contains a gelling agent which forms a stable hydrogel after the filling, as a result of which the incorporated cells or cell spheroids are immobilized. Use can be made of enzymatically crosslinking gels (e.g. fibrin), physically crosslinking gels (e.g. collagens) or photopolymerizable or photocrosslinkable liquids as the material basis for the gelling agent.

In further embodiments, the colonization chamber is preferably colonized using a tissue resection or a biopsy (so-called ex vivo culture). In further embodiments, the tissue resection/the biopsy can be glued in place with a gel-forming liquid.

A 3D scaffold according to the invention is preferably produced by a lithographic 3D printing method, preferably a stereolithographic 3D printing method. By a stereolithographic 3D printing method it is meant one in which the structure of the 3D scaffold is produced gradually by curing photopolymerizable or photocrosslinkable substances in layers. In this case, the photopolymerizable or photocrosslinkable substances are used in the form of photopolymerizable or photocrosslinkable liquids. The construction of a 3D scaffold comprising a biocompatible polymer using a stereolithographic 3D printing method offers the possibility of printing a biocompatible polymer in a physiological shape, such that material and architecture resemble the structure in the human body to be simulated. Since the biological cells can only subsequently be introduced into the 3D scaffold for colonization, it is possible to construct a 3D cell culture construct of any cell type in a 3D scaffold according to the invention.

The present invention thus also relates to methods for producing a 3D scaffold according to the invention by curing a photopolymerizable or photocrosslinkable substance by focusing an electromagnetic radiation in a focal plane in which the photopolymerizable or photocrosslinkable substance is present. Preferred embodiments of the method are described further below.

During the production of a 3D scaffold in accordance with the present invention, the curing of a photopolymerizable or photocrosslinkable substance is preferably achieved by focusing an electromagnetic radiation in a focal plane in which the photopolymerizable or photocrosslinkable substance is present. Preferably, in this case, the photopolymerizable or photocrosslinkable substance is present in liquid form, for example dissolved in a solvent. Hereinafter, reference will be made to a photopolymerizable or photocrosslinkable liquid.

By repeating the focusing of a further electromagnetic radiation in a further focal plane using a further photopolymerizable or photocrosslinkable liquid, a 3D scaffold according to the invention can be constructed.

Methods for producing the 3D scaffold according to the invention is described in more detail further below.

The term "photopolymerizable" is used herein to mean that the corresponding substance can be polymerized by the action of electromagnetic radiation and optionally the presence of a photoinitiator. By "photocrosslinkable" it is likewise meant that an oligomer or polymer can be crosslinked by the action of electromagnetic radiation and optionally the presence of a photoinitiator.

A 3D scaffold according to the invention can be constructed from a homogeneous material and consequently only comprise a biocompatible polymer of a single type. In some variants, the 3D scaffold can be constructed from different biocompatible polymers, i.e. is a heterogeneously constructed 3D scaffold. In this case, at least two different photopolymerizable or photocrosslinkable liquids are used in the production thereof. It is possible in this way to achieve different polymer structures within the 3D scaffold. Thus, for example, the region between the colonization chamber and the canal-type vessel can be surrounded by a polymer structure which differs from the polymer structure of the remaining scaffold of the 3D scaffold, in order for example to have a larger porosity which enables the penetration of nutrients of a nutrient-containing liquid from the canal-type vessel into the colonization chamber.

The colonization chamber can also have columns, grids or crosspieces in order to enable the biological cells to adhere to its inner surface.

The properties of the polymer structure or the various polymer structures within the 3D scaffold can be influenced by the choice of the monomers to be polymerized or the polymers to be crosslinked in the photopolymerizable or photocrosslinkable liquid(s). The lower the molecular weight of the polymerizable or crosslinkable units, generally speaking the smaller the interstices or pores of the resulting matrix of the 3D scaffold are. However, the last-mentioned case is also heavily dependent on the number of crosslinkable units in the polymers and therefore the degree of crosslinking. The higher the degree of crosslinking, generally speaking the smaller the interstices or pores of the resulting matrix of the 3D scaffold are. In principle, the lithographic 3D printing method makes it possible to use different polymer or monomer solutions in each layer in order to obtain a 3D scaffold with a high level of complexity or diversity.

In other words, it is preferred according to the invention that a 3D scaffold according to the invention is constructed from a first biocompatible polymer and at least one further biocompatible polymer which is different from the first biocompatible polymer. In one variant of the 3D scaffold according to the invention, it is furthermore preferred that the region between colonization chamber and canal-type vessel contains the at least one further biocompatible polymer.

Due to the different focal planes in which a polymerization or crosslinking of the photopolymerizable or photocrosslinkable liquids takes place a layered construction of the 3D scaffold can be achieved. In this case, it is possible to form covered cavities, such as the canal-type vessel, in the 3D scaffold. Furthermore, undercuts and overhanging structures can also be formed, since a polymerization or crosslinking of the photopolymerizable or photocrosslinkable liquid can also be effected in a specific focal plane or layer if there is no already polymerized or crosslinked material arranged thereunder but rather only as yet unpolymerized or uncrosslinked liquid. A polymerization or crosslinking of a photopolymerizable or photocrosslinkable liquid present outside the focal plane does not take place; rather, only the photopolymerizable or photocrosslinkable liquid lying within the focal plane is polymerized or crosslinked. Nonetheless, the liquid present outside the focal plane serves to temporarily support the liquid present in the focal plane, without solid support structures being necessary for this purpose.

In some designs of a 3D scaffold according to the invention, it is preferred that the filling opening(s) is (are) arranged on the top side of the 3D scaffold. This has the advantage that the 3D scaffold can be filled directly from above with a cell suspension. The filling opening(s) is (are) preferably arranged at the edge of the upper surface of the 3D scaffold. The filling opening(s) is (are) preferably formed as a filler neck. For this, it is preferred that a hollow-cylindrical or hollow-prismatic neck is fitted onto the preferably round filling opening. This makes it easier to insert a pipette tip and to fill the canal-type vessel with cell suspension.

In some designs of a 3D scaffold according to the invention, it is preferred that the outlet opening(s) is (are) arranged on the side of the 3D scaffold. This makes it possible for the outlet opening(s) to be arranged at a lower point than the filling opening, with the result that liquid already present in the canal-type vessel can be displaced through the filling with a cell suspension. A 3D scaffold according to the invention preferably has two outlet openings, which are arranged on opposite sides of the 3D scaffold.

A 3D scaffold according to the invention preferably has a flat shape, i.e. is preferably larger in its horizontal dimensions than in the vertical dimension. Such 3D scaffolds can have any footprint, such as for example circular, oval, rectangular or square, the latter two also having rounded corners, wherein a rectangular or square shape is preferred. Preferably, the 3D scaffold extends vertically prismatically, i.e. the footprint does not substantially change in the vertical direction. The diameter is preferably in the range from 100 μm to 10 cm. The height is preferably in the range from 100 μm to 10 cm. The shape of the canal-type vessel can be round, oval or angular in cross section, preferably round, with a diameter in the range from 1 μm to 2 cm. The colonization chamber preferably has a diameter in the range from 10 μm to 8 cm. The volume of the colonization chamber is preferably in the range from 1 μl to 50 ml.

As already mentioned further above, in some designs of the invention the 3D scaffold is one which is obtainable with the aid of a lithographic 3D printing method.

These 3D printing methods are described in more detail in the following:

The production of a 3D scaffold according to the invention is preferably divided into the following method steps:

(I) introducing a photopolymerizable or photocrosslinkable liquid into a reaction vessel, (II) focusing an electromagnetic radiation on a focal plane which lies within a region of the reaction vessel filled with the liquid, (III) producing a polymerized or crosslinked structure in a layer of the focal plane in the reaction vessel through the electromagnetic radiation, (IV) introducing a further photopolymerizable or photocrosslinkable liquid into the reaction vessel, with the result that a previously produced polymerized or crosslinked structure is at least partially covered with the further photopolymerizable or photocrosslinkable liquid, (V) focusing a further electromagnetic radiation on a further focal plane which lies within a region of the reaction vessel filled with the further liquid, (VI) producing a further polymerized or crosslinked structure in a further layer in the reaction vessel through the further electromagnetic radiation, wherein the further polymerized or crosslinked structure is arranged directly on the previously produced polymerized or crosslinked structure and is bonded thereto, (VII) repeating steps (IV) to (VI) with a further photopolymerizable or photocrosslinkable liquid in each case, until the 3D scaffold has been produced.

The further focal plane in step (V) preferably differs from the first focal plane at least with respect to the already produced polymerized or crosslinked structure or with respect to the layer of this polymerized or crosslinked structure.

The bonding of the polymerized or crosslinked structures produced in step (VI) is preferably bonding through covalent bonds. However, non-covalent bonds, for example those based on physical interactions, are also possible.

One or more of the photopolymerizable or photocrosslinkable liquids used in the production method can contain biological cells. If a polymerization or crosslinking occurs as a result of the irradiation by the electromagnetic radiation, the cells contained in the liquid will also be embedded in a corresponding polymer. However, it is preferred according to the invention that no biological cells are used in the lithographic 3D printing method, so that the 3D scaffold can be easily stored, before the subsequent colonization can be effected by the user.

Cavities (so-called wells) of commercially available microtiter plates (for example microtiter plates having 6, 12, 24, 48, 96, 384 or 1536 cavities), cell culture flasks or Petri dishes can be used as reaction vessels in a method for producing the 3D scaffold according to the invention.

In further designs, a 3D scaffold according to the invention is one which is transparent at least in the visible light range. This makes it possible to optically track and record the subsequent colonization with biological cells.

The photopolymerizable or photocrosslinkable substance in the photopolymerizable or photocrosslinkable liquid is preferably one having a photoreactive group which can form covalent bonds with further photoreactive groups.

In some variants, the photoreactive group is an acrylic group, by means of which the polymerization or crosslinking is carried out. That is to say the photopolymerizable or photocrosslinkable substance is preferably an acrylic compound, for example one from the following group: methacrylates, methyl acrylates, ethyl acrylates, hydroxyethyl acrylates, butyl acrylates, trimethylolpropane acrylates, triacrylacrylates and polyacrylates (PA) in general.

The substance to be polymerized or crosslinked can be a polymer, an oligomer or a monomer. Preferably, these are carbon-based substances. In the case of monomers, photopolymerization is carried out. In the case of polymers or oligomers, photocrosslinking is preferably carried out.

As monomers to be polymerized, the following can for example be used: acrylamides, vinyl chloride, ethylene, propylene, isoprene, caprolactam, all amino acids, (de)oxyribonucleotides, glucose, and all monosaccharides, as well as the abovementioned acrylates.

As oligomers or polymers, the following can be used: polyethylene glycol (PEG), polyethylene (PE), polypropylene (PP), polyketone (PK), polyvinyl chloride (PVC), polystyrene (PS), polytetrafluoroethylene (PTFE), polymethyl methacrylate (PMMA), polycarbonate (PC), polyethylene terephthalate (PET) and polyurethane (PU). Further, synthetic polymers such as silicones, polydimethylsiloxane (PDMS) or resins such as for instance melamine or melamine-formaldehyde resins are suitable as starting substance. Further, biopolymers such as for instance proteins, DNA, RNA, carbohydrates and carbohydrate derivatives, collagens, fibrins, alginates, gelatins, hyaluronic acids or polylactides are suitable as starting substances. Instead of the abovementioned polymers, it is also possible in each case to use the monomer precursors or oligomer precursors of these polymers as starting substances, as long as these can be stably provided in the solid or liquid state. The introduction of a photoreactive group, for example an acrylic group, into the starting substance makes the latter photopolymerizable or photocrosslinkable. The radiation-induced coupling of the acrylic radicals between various molecules of the starting substance produces a polymerized or crosslinked matrix.

If photopolymerizable PDMS is used as matrix or as enveloping substance, a gas exchange between the cells embedded in this matrix is possible. As already mentioned, different enveloping substances or matrices can be used. Thus, for example, aside from PDMS or another matrix which has good biocompatibility, it is possible to use a stable plastic for the rest of the matrix, in order in this way to produce an outwardly stable object, the interior of which contains a matrix which enables cell growth and has lower stability.

The starting substance supplemented by the photoreactive group is used in a liquid form, with different viscosities being possible. That is to say, methods for producing the 3D scaffold according to the invention is not restricted to photopolymerizable or photocrosslinkable liquids with a specific viscosity; rather, low-viscosity liquids can also be used. Both Newtonian and non-Newtonian fluids can be used.

The liquids can be solutions or colloidally dispersed mixtures, such as for instance suspensions. In this case, the liquids can have an aqueous to oily character. This is determined inter alia by the choice of the starting substances and the particle sizes thereof.

In order to be able to achieve a photopolymerization or photocrosslinking of the starting substance bearing a photoreactive group, a radical former (a so-called photoinitiator) is also preferably used, which forms radicals at a selected wavelength of the electromagnetic radiation used in the context of the method.

Suitable radical formers are, for example, anthrone derivatives such as for instance violanthrone or isoviolanthrone, fluorescein, rubrene, anthrazine derivatives, tetrazene derivatives, benzanthrone, benzanthronil, eosin, levolinic acid derivatives, phosphine derivatives, mono- and bis-acylphosphines, metallocenes, acetophenones, benzophenones, xanthones, quinones, ketone derivatives, hydroxy ketones, amino ketones, benzoyl peroxides, pyridine salts, phenylglyoxylates and/or iodonium salts.

In addition to the radical former, use is preferably also made of a vinyl macromer and an amine-based co-initiator, in order to enable the photopolymerization or photocrosslinking to proceed in a particularly suitable manner. Ascorbic acid and tertiary amine derivatives, such as for instance methyl diethanolamine or tetraethylamine, are suitable for example as co-initiator.

In some variants, the photopolymerizable or photocrosslinkable liquid contains a thiol derivative. Suitable thiol derivatives are dithiothreitol, monofunctional cysteines, bifunctional peptides and similar compounds.

Moreover, a substance can be added to the photopolymerizable or photocrosslinkable liquid which prevents a photopolymerization or photocrosslinking of deeper liquid layers. Thus, liquid solution outside the focal plane remains liquid, even if it is located in the irradiation region of the focal plane lying over it. This functions by absorption of the substance at the wavelength at which the polymerization takes place (polymerizing wavelength). The capture takes place in the focal plane, with the result that it is not possible for the polymerizing wavelength to penetrate into deeper layers. All substances which absorb in the desired wavelength, such as for instance dyes, are suitable.

Moreover, in some variants, it is possible for the one photopolymerizable or photocrosslinkable liquid and/or one of the further photopolymerizable or photocrosslinkable liquids and/or another liquid which does not have to be photopolymerizable to contain a temperature-sensitive gelling agent. Provision is particularly made for the use of an inversely temperature-sensitive (also referred to as reverse temperature-sensitive) gelling agent. Such a gelling agent becomes increasingly solid with rising temperature. By heating the reaction vessel, the reaction liquid solidifies and forms a gel which is initially only metastable. If the liquid is not simultaneously photopolymerized or photocrosslinked, the metastable gel can be re-liquefied by subsequent cooling of the 3D scaffold and pumped out. In the case of customary temperature-sensitive gelling agents, the temperature ratios to be applied are exactly the opposite. Thus, for example, as required, a support structure can be created, with the result that hanging structures can be produced. If, on the other hand, the metastable gel is at least partially irradiated with electromagnetic radiation at a suitable wavelength, this leads to a photopolymerization, with the result that the metastable gel in these regions is converted into a stable gel or polymer.

In other words, the temperature-sensitive, particularly inversely temperature-sensitive, gelling agent and the control of the temperature of the reaction chamber make it possible to work even more simply with hanging parts and undercuts or cavities. In this variant, too, it is possible also to work with liquid structures as support.

Moreover, it is possible to provide a temperature gradient, with the result that a metastable gel does not arise in all regions of the liquid which has the temperature-sensitive, particularly inversely temperature-sensitive, gelling agent added to it. Using such a gradient makes it possible to produce even more complex structures.

The abovementioned individual components can be present as individual substances in the photopolymerizable or photocrosslinkable liquid. Alternatively, it is also possible to produce the substances or groups preferably used for gel formation in a single polymer by corresponding synthesis. Instead of a mixture of individual components, such a polymer would then have different functional groups, which bring together all the functions required, or preferably to be used, for a photopolymerization or photocrosslinking. Further, it is also conceivable to provide just some of the functions or groups preferably used for the photopolymerization or photocrosslinking in one polymer, and to add other functions or groups preferably to be used for the photopolymerization or photocrosslinking in separate individual components of the photopolymerizable or photocrosslinkable liquid.

Alternatively or additionally to the formation of cavities or canal-type vessels by using a gelling agent, enzymes can also be used to digest the polymer. The principle is as follows: a 3D scaffold with cavities/undercuts (e.g. a canal system) is printed as a solid body, with all the cavities being filled with a sacrificial material during printing, which can be dissolved later (i.e. after conclusion of the printing) by adding the correct enzyme. The sacrificial material is for example a digestible polymer which is digested by adding a digesting enzyme. This is an elegant strategy for creating cavities with stereolithographic printing methods. For example, a hyaluronidase (digesting enzyme) can digest hyaluronic acid (sacrificial material), with the result that a cavity is formed at the location in the 3D scaffold where the hyaluronidase is used. This principle has already been described in the patent application having the official file number DE 10 2019 200 792.9. Alternatively, to create a cavity/undercut, a photoblocker can also be used in the photopolymerizable or photocrosslinkable liquid, wherein the photoblocker restricts the depth of cure of the photopolymerizable or photocrosslinkable liquid.

In some variants, the further photopolymerizable or photocrosslinkable liquid is only introduced into the reaction vessel when the photopolymerizable or photocrosslinkable liquid previously located in the reaction vessel (this can for example be the one photopolymerizable or photocrosslinkable liquid or a further photopolymerizable or photocrosslinkable liquid) has been removed from the reaction vessel.

In some variants, the 3D scaffold, during or at the end of the process for producing same, can be irradiated with electromagnetic radiation of a short wavelength (for example in the UV range, i.e. below 380 nm), in order thereby to achieve a sterilization.

In some variants, a carrier plate or carrier structure to which the first polymerized or crosslinked structure is bonded is arranged in the reaction vessel. The use of such a carrier plate is expedient if the 3D scaffold produced is not to be investigated at a later time in the reaction vessel itself, but rather is to be removed from the reaction vessel. In the carrier plate, screw connections (such as for instance DIN screw connections), for example, can be present in order to enable a subsequent supply of liquids and gases to the 3D scaffold produced. It is also possible to introduce such screw connections into the matrix of the 3D scaffold as part of the production method, i.e. to produce these screw connections there in the matrix. The production of such screw connections in the matrix can be undertaken regardless of whether or not a carrier plate is used.

In some variants, a carrier plate is produced, before the step of producing a first polymerized or crosslinked structure by irradiation with an electromagnetic radiation in a focal plane lying within a region of the reaction vessel filled with a photopolymerizable or photocrosslinkable liquid (in particular with the first or one of the further photopolymerizable or photocrosslinkable liquids), by forming a polymerized or crosslinked carrier structure which has or constitutes the carrier plate. This means that, in these variants, not only the actual polymerized or crosslinked structures, but also the carrier structure, are produced by a polymerization or crosslinking reaction.

The carrier structure can have a shape such that a gap is formed between the carrier plate and a base of the reaction vessel. As a result, the focal planes of the actual polymerization or crosslinking reactions then have a larger gap from the base of the reaction vessel. The first formed polymerized or crosslinked structure then particularly has a larger gap from the base of the reaction vessel. Polymerizable or crosslinkable liquids which are no longer required can then be particularly easily suctioned off from the reaction vessel.

In some variants, an optical system which serves to focus the electromagnetic radiation on the respective focal plane in the reaction vessel is arranged between a source for the electromagnetic radiation (radiation source), which serves to generate the one and/or the further electromagnetic radiation, and the reaction vessel. In this case, in some variants it is provided that a refocusing of this optical system can take place in order to change the focal plane within the reaction vessel. Such a refocusing can be achieved for example by changing the gap between the optical system and the radiation source. In this case, a computer-controlled stepper motor can be provided in order to facilitate a corresponding movement of the optical system. The optical system can for example be a system of optical lenses or—in a construction supported in a particularly simple manner—an individual focusing lens.

In some variants, it is also possible to carry out a relative movement between the reaction vessel or a carrier plate arranged in the reaction vessel on the one hand and the radiation source which serves to generate the one and/or the further light radiation on the other hand. This is because a relative movement of this kind, which can for example be effected by a movement of the reaction vessel, by a movement of the carrier plate arranged in the reaction vessel or by a movement of the radiation source, also makes it possible to change the focal plane within the reaction vessel. As a result, in these variants, no refocusing of an optical system optionally to be used is required. This makes it possible to reduce the risk of optical misalignment.

In further variants for producing the 3D scaffold according to the invention, the one and/or the further electromagnetic radiation is directed onto a defined and predeterminable region in the respective focal plane within the one photopolymerizable or photocrosslinkable liquid and/or the further photopolymerizable or photocrosslinkable liquid. That is to say, a specific radiation pattern can be specified which impinges on the photopolymerizable or photocrosslinkable liquid and at these locations serves to polymerize or crosslink the liquid to form a polymer or a gel (the matrix). Such a radiation pattern can for example be produced using masks or collimators, but also using pulsed radiation or by digitally modulating a radiation signal. At the regions of the photopolymerizable or photocrosslinkable liquid impinged upon by the radiation, a polymerization or crosslinking takes place. At the other regions that are not impinged upon by the radiation, however, the photopolymerizable or photocrosslinkable liquid remains in its unpolymerized or uncrosslinked state. Thus, the radiation defines the regions where a printing of the polymerized or crosslinked structure occurs. Such a radiation-assisted printing makes much higher resolutions possible than is the case in the methods known from the state of the art. In this case, the resolution is dependent on the wavelength of the radiation used. Even at the commonly used long wavelengths, it is better than the resolution which can be achieved with the conventional methods known from the state of the art. The more precisely the radiation source can be focused, the higher the resulting resolution. For example, very high resolutions can be achieved with a laser.

The irradiation pattern selected in each case can be provided for example by a computer program. It is thus conceivable for a user to create the 3D scaffold to be produced by means of a CAD program. The digital object created in such a way is then cut up into individual irradiation planes by a suitable computer program. Further, each plane or different locations in each plane is assigned a specific photopolymerizable or photocrosslinkable liquid. With regard to this information, control information is created for a printer, by means of which the described method is carried out. This control information specifies when and which photopolymerizable or photocrosslinkable liquid has to be introduced into the reaction vessel. Further, this control information specifies when and which image of an irradiation plane is to be projected onto the respective focal plane in the reaction vessel. This makes it possible to then convert the 3D scaffold created beforehand on a computer into a real 3D scaffold.

In some variants, more than one polymerized or crosslinked structure is produced in the same layer (i.e. in the same focal plane). To this end, a polymerization or crosslinking of a first photopolymerizable or photocrosslinkable liquid is first effected. Then, the first photopolymerizable or photocrosslinkable liquid is removed from the reaction vessel and a second photopolymerizable or photocrosslinkable liquid is introduced into the reaction vessel. Now, only those regions within the focal plane in the reaction vessel which were not previously irradiated and where there is consequently not yet any polymerized or crosslinked structure are irradiated. As a result, different matrices can be produced in one and the same layer. Consequently, a plurality of polymerized or crosslinked structures are formed in one and the same layer, thus resulting in a heterogeneous layer. Then, the second photopolymerizable or photocrosslinkable liquid can be removed from the reaction vessel and a further photopolymerizable or photocrosslinkable liquid can be introduced into the reaction vessel. The filling level of this further photopolymerizable or photocrosslinkable liquid can now be brought to a level such that the previously formed layer is completely covered. The focal plane can then be displaced, and a further layer of the 3D scaffold to be produced can be constructed by a corresponding polymerized or crosslinked structure. It is in principle possible in this case for individual layers of the 3D scaffold produced to be homogeneous (comprising a polymerized or crosslinked structure of a single type) and other layers to be heterogeneous (comprising polymerized or crosslinked structures of different types), wherein the number of individual structures per layer is unlimited. In practice, besides a single polymerized or crosslinked structure per layer, heterogeneously composed layers having 2, 3, 4, 5, 6, 7, 8, 9 or 10 polymerized or crosslinked structures have proved to be useful.

In some variants, at least the first structure of the first layer, but particularly each structure of the first layer, is irradiated with the first radiation from two different directions. In this case, these two different directions are preferably opposite one another. Such an irradiation from two different directions achieves particularly secure anchoring of the first layer to the inner surface of the reaction vessel or to a carrier plate arranged in the reaction vessel. As a result, a subsequent secure holding, of the whole 3D scaffold produced, on the reaction vessel or on a carrier plate in the reaction vessel is achieved, as a result of which subsequent investigations on the 3D scaffold can be made easier. Typically, the irradiation is effected from above in the case of a reaction vessel which is open at the top. In these variants, the first layer is then preferably additionally irradiated from below, through the base of the reaction vessel. To this end, the reaction vessel must be manufactured from a material which is permeable to the radiation with the selected wavelength. The subsequent layers arranged above the first layer are then preferably in turn only exposed to light from one direction (namely preferably from above), so that the already formed polymerized or crosslinked structures do not lie between the focal plane of the radiation and a radiation source used for emitting the radiation, and therefore are not shone through again by the radiation before their focal plane.

In some variants, the first electromagnetic radiation and/or the further electromagnetic radiation have a wavelength in the range from 200 nm to 1000 nm (i.e. a wavelength lying between the UV range and the infrared range), more preferably in the range from 350 nm to 800 nm. Such wavelengths make it possible to particularly successfully excite the substances preferably used as radical formers such that radicals are formed, in order to enable a polymerization or crosslinking of starting substances bearing acrylic radicals.

Further suitable wavelengths of the electromagnetic radiation used are in the range from 250 nm to 950 nm, particularly from 250 nm to 850 nm, particularly from 300 nm to 800 nm, particularly from 300 nm to 750 nm, particularly from 300 nm to 700 nm, particularly from 350 nm to 650 nm and quite particularly from 350 nm to 400 nm.

The radiations used for the polymerization or crosslinking can comprise the same wavelength or else different wavelengths from the abovementioned wavelength range, in order to enable a suitable polymerization of the different photopolymerizable or photocrosslinkable liquids. In this case, the individual radiations can be generated using different radiation sources or else using one and the same radiation source. It is also possible to use successively different wavelengths within a layer (and thus within a focal plane) in order to polymerize or crosslink different photopolymerizable or photocrosslinkable liquids in the same layer, if a heterogeneous layer is to be formed from different polymerized or crosslinked structures.

In some variants, the method is carried out such that, during the production of the 3D scaffold, at least one functional element is introduced into the 3D scaffold. The functional element here is selected from the group consisting of membranes, channels, pores, sensors, columns, grids, lattices, crosspieces, or electrically conductive carriers and chemotactic preparations. Channels and pores can for example be integrated into the object by specific regions of the polymerized or crosslinked structure formed being left open in a plurality of layers one above the other. Membranes can be formed by introducing lipid molecules into the photopolymerizable or photocrosslinkable liquid.

Moreover, salt bridges can also be introduced within the 3D scaffold by means of the photopolymerization or photocrosslinking. This is particularly readily possible if the photopolymerizable or photocrosslinkable liquid contains salts, i.e. is saliferous. In this way, electrical discharge and enervation of the printed 3D scaffold can subsequently take place.

Via sensors already introduced into the 3D scaffold during the production process, the 3D scaffold produced no longer needs to be subsequently manipulated, but rather can be read out directly via the sensors already introduced. This considerably facilitates subsequent analyses of the 3D scaffold colonized with biological cells. For example, by introducing electrically conductive carriers, such as for instance electrodes, it becomes particularly simple to analyze the electrical potential or the electrical properties of the colonized 3D scaffold during a subsequent investigation of the 3D scaffold formed.

By introducing chemotactic preparations, which in some variants can be introduced in different concentrations in different layers in order thus to produce a gradient, the targeted growth/colonization of biological cells within the 3D scaffold after completion thereof can be made possible. If the chemotactic preparation is an attractant, it exerts positive chemotaxis, with the result that the biological cells in the 3D scaffold will orient themselves toward regions of higher concentration of the attractant. If, however, the chemotactic preparation is a repellent, it exerts negative chemotaxis, with the result that the biological cells in the 3D scaffold will orient themselves toward regions of lower concentration of the repellent or toward regions where the repellent is entirely absent. As a result, a targeted growth/colonization of cells can be achieved within the 3D scaffold.

Preferably, at least one filling level sensor is used in order to always precisely identify the liquid level in the reaction vessel. Using this filling level information, the focal plane in which the next polymerization or crosslinking step is to be carried out can then be determined. The data provided by such a filling level sensor can also serve to automatically adapt the focal plane. The data provided by a filling level sensor can also be used to control a pump which facilitates the flow of the photopolymerizable or photocrosslinkable liquids into the reaction vessel. This makes it possible to always introduce precisely the amount of the photopolymerizable or photocrosslinkable liquids into the reaction vessel which is required for constructing precisely the desired layer. As a result, waste is kept to a minimum. Further, this enables the entire method to be carried out cost-effectively.

The step of 3D printing the 3D scaffold can be carried out entirely automatically, with the result that intervention by a user is not required. This additionally facilitates implementation of the methods.

The duration for which the electromagnetic radiation is irradiated onto the respective focal plane can be adapted to the respective requirements of the photopolymerizable or photocrosslinkable liquids used. That is to say, each material is accorded a time for the curing such as is required and useful for the desired polymerization or crosslinking.

If a carrier is arranged within the reaction vessel, a negative pressure can arise between a surrounding liquid bed and the already polymerized or crosslinked structures on the carrier when said carrier is raised relative to the reaction vessel. However, a potentially prevailing negative pressure can be relieved by suctioning off the radicals of the photopolymerizable or photocrosslinkable liquid remaining in the reaction vessel for the previous polymerization or crosslinking step and introducing a new photopolymerizable or photocrosslinkable liquid. As a result, the carrier can be moved relative to the reaction vessel without needing to worry about tearing the already polymerized or crosslinked structures of the 3D scaffold off the carrier.

If the 3D scaffold is produced on a carrier plate, this carrier plate can be completely lifted out of the remaining liquid in the reaction vessel after the end of the production process. The 3D scaffold produced can subsequently be removed from the carrier plate by the user.

To produce a 3D scaffold according to the invention, it is possible for example to use a 3D printing device, such as is described in EP 3 018 531 A1.

By adding a temperature-sensitive, particularly an inversely temperature-sensitive, substance, the production of hanging objects and cavities in the 3D scaffold can additionally be improved. In this case, for example, a substance such as for instance a poloxamer can be added in a concentration such that the photopolymerizable or photocrosslinkable liquid or a non-photopolymerizable or non-photocrosslinkable liquid also gels, without irradiation, in a desired temperature range.

For example, a method in accordance with the invention can proceed as follows: if gelling is to be achieved at a temperature of approx. 20° C. (for example to be referred to as the "gelling temperature"), a poloxamer is mixed into the photopolymerizable or photocrosslinkable liquid in a concentration such that the liquid gels in this region. Mixtures of a plurality of poloxamers are also possible. If possible, the liquid can first be cooled to a temperature below the gelling point. If a hanging structure is desired within the object, the liquid containing the temperature-sensitive gelling agent can be heated to a temperature which lies above the gelling temperature. The liquid then gels. In parallel thereto, the liquid can also be photopolymerized or photocrosslinked. If a region of the temperature-sensitive liquid is not photopolymerized or photocrosslinked, although the liquid is solid at the increased temperature, it can be re-liquefied at any time when the temperature is lowered to below the gelling temperature. Thus, the temperature-sensitive gelled part can act as a support structure until the end of the printing process. After completion of the printing, the temperature can again be lowered to below the abovementioned gelling temperature of for example 20° C. As a result, the unpolymerized or uncrosslinked temperature-sensitive part of the liquid re-liquefies and can be pumped out. If the gel is liquefied, the support structure is removed and the previously supported part of the printed object, which is now photopolymerized or photocrosslinked, hangs free.

In some design, the present invention also relates to a 3D scaffold according to the invention, the colonization chamber of which is at least partially colonized with biological cells. In other words, the present invention therefore also relates to the use of a 3D scaffold according to the invention for colonizing the colonization chamber with biological cells, in particular for the colonization with biological cells which are supplied with nutrients within the 3D scaffold. In other words, the present invention also relates to methods for colonizing the cavity of a 3D scaffold according to the invention, wherein a cell suspension is introduced into the cavity, wherein the biological cells introduced by the cell suspension are supplied with nutrients.

The present invention also relates to the use of a 3D scaffold according to the invention for culturing biological cells to form a tissue or organ in the colonization chamber thereof, i.e. for producing a 3D cell culture construct. In other words, the present invention also relates to a method for producing a cell culture construct, or tissue or organ, by culturing biological cells in the colonization chamber of the 3D scaffold. The culturing conditions are dependent on the type of cells used. A person skilled in the art in the field of biology generally knows the ideal culturing conditions for various biological cells. The culturing conditions to be determined on the basis of the cell type are temperature, composition of the respective nutrient solution, and nature of the culture vessel. By way of example, mention can be made here of the conditions for human blood vessel cells from the umbilical cord: 37° C., minimal medium with glucose, all essential amino acids, vitamins and minerals. Here, the culture is preferably in Petri dishes or cell culture flasks which have been coated for tissue cultures (so-called tissue culture-treated surfaces). Said culture conditions are advantageous for numerous human cells. In the case of vascular cells, the use of growth factors which are added to the minimal medium is additionally necessary.

Subsequently, the 3D cell culture construct can be penetrated by further cells, viruses, bacteria, enzymes or active substances, in order to perform tests on the construct. To this end, the filling opening(s) or the opening of the colonization chamber can be used, but some substances or cells can thus also penetrate the material of the 3D scaffold. In this way, for example, tumor cells can be attacked by CAR-T cells.

In some designs of the 3D scaffold according to the invention, the 3D scaffold is present in dry form, i.e. the 3D scaffold is dried after the process of lithographic 3D printing. This gives the 3D scaffold a more durable form which is better for transporting. After completion of the drying/vitrification, the 3D scaffold can be stored for at least six weeks in a refrigerator, protected from light and moisture. In the process, the 3D scaffold shrinks slightly and becomes harder. Wet storage puts the 3D scaffold at risk of deteriorating more quickly. The drying/vitrification is preferably carried out in a sterile environment. Suitable drying temperatures are in the range from 4° C. to 50° C., more preferably in the range from 15° C. to 25° C. The drying can for example be carried out in a drying cabinet, in a climatic chamber or the like.

All naturally occurring eukaryotic and prokaryotic cells are suitable as biological cells which are used for constructing the 3D scaffold colonized with biological cells. The cells used are preferably eukaryotic cells. All cells and cell types occurring in, or forming, the body of a mammal, in particular a rodent and quite particularly a human, are particularly suitable. In some variants, the biological cells used are omnipotent or pluripotent cells. In this case, in some variants, the invention only relates to the use of such cells which can be obtained without the destruction of human embryos. In addition to naturally occurring cells, cells of non-naturally occurring cell lines can also be used as biological cells. Such artificially generated cell lines enable the custom construction of a 3D cell culture construct or three-dimensional multicellular object to be produced.

Since a scaffold according to the invention enables the combination of different cell types to form a 3D cell culture construct, it is particularly suitable for producing artificial organs. Such artificial organs can for example be miniaturized model objects of a naturally occurring organ, particularly a naturally occurring organ of a human or an animal, such as for instance a mammal or a rodent. It is also possible to combine plastic polymers and biopolymers, with the result that highly stable structures can be produced, in which the biological cells are embedded. During a single printing process, a plurality of 3D scaffolds, even with different forms, can be produced at the same time.

In order for the user to be able to use the dried 3D scaffold according to the invention for the colonization with biological cells, the 3D scaffold is rehydrated. For this, the 3D scaffold is preferably placed in water, a salt solution, a buffer, cell medium or a similar physiologically acceptable liquid, preferably for a period of 60 s to 60 min. Ideally, this treatment is effected in a Petri dish or similar under sterile conditions. As a result, the scaffold regains its original size, strength and nature.

To colonize the scaffold with biological cells, a suspension comprising biological cells and a desired solvent is preferably mixed. All solutions compatible with cells can be used as solvent. This comprises all aqueous solutions which ensure cell survival. Usually, substances are used to set a neutral pH (pH 7.4) and an isotonic environment, in order to approximate the fluids in the human body (e.g. blood) with the solutions. The concentration of the biological cells in the solvent is preferably in a range from 100,000 to 300,000,000 cells per milliliter. For the colonization of the 3D scaffold, the cell suspension is preferably introduced into the scaffold via the filling opening or into the colonization chamber. In this case, it is preferred that the total volume of the cell suspension to be filled is at most as large as the volume of the respective cavity (colonization chamber or canal-type vessel) of the 3D scaffold. If the desired cell concentration has been set, the user can flush the volume into the scaffold, for example using a pipette.

When colonizing with biological cells, possible columns, grids or crosspieces in the colonization chamber of the 3D scaffold can act as an anchor or retainer for the biological cells, with the result that they can adhere to the 3D scaffold.

After the 3D scaffold has been filled with the cell suspension, the construct which now contains cells can be cultured further. Depending on the internal construction of the cavity, a new 3D cell culture model can now form. In the case of adherent cells, the biological cells adhere to all available structures and to each other, with the result that a 3D structure in the shape of the cavity of the 3D scaffold is formed.

In this way, a 3D cell culture model/construct is formed in a controlled manner. If the 3D scaffold is to be colonized for example with tumor cells, a 3D tumor model is formed.

A 3D scaffold according to the invention makes it possible to produce complex biological 3D cell culture constructs as models in order to represent and investigate, for example, cell-cell interactions, organ biogenesis, diseases or organ functions. Such a 3D cell culture construct has considerable advantages compared to the conventional two-dimensional cell culture, in particular regarding modeling the interaction of several cell types. This is because the complexity of cell-cell interactions, the function of a natural barrier and the modeling of diseases or organs cannot be sufficiently reproduced using conventional two-dimensional cell cultures.

Moreover, the 3D scaffold according to the invention makes it possible to create miniaturized models particularly simply. Such miniaturized models have hitherto been constructed manually in some cases. The effort required for this is extremely high; in addition, many years of experience are necessary.

Finally, the colonization of a 3D scaffold according to the invention with cells makes it possible to guarantee a high degree of reproducibility of different copies of the same 3D cell culture construct. The use of a 3D scaffold additionally enables the targeted construction of a 3D cell culture. Consequently, not only does the use of a 3D scaffold according to the invention make it possible to accelerate production compared to other methods known from the state of the art, but the 3D cell culture constructs produced also always have the same quality. Such a high degree of reproducibility is particularly advantageous in biotechnology. This is because, when analyzing and developing new pharmaceutical products, testing on constantly consistent three-dimensional cell cultures significantly reduces the development costs. On the contrary, if such complex three-dimensional structures are constructed manually, individual variations are inevitable. This makes it virtually impossible to obtain reproducible test results. In contrast, the use of a 3D scaffold according to the invention provides 3D cell culture constructs which are exceptionally well-suited to producing reproducible test results.

The present invention has the following advantages: scaffolds with undercuts or complex architectures which can be colonized by a user themselves were hitherto not possible. The 3D scaffold itself functions as a hollow body, the production of which hitherto would not have been possible without multi-material stereolithography. The complex architecture which influences the behavior of the cells could not be reproduced in this way. The production route according to the invention makes it possible to ensure a high degree of reproducibility and parallelism. Despite a complex architecture, the 3D scaffold can be reproduced accurately to the millimeter. Moreover, the system allows, for the first time, the production of vascular structures. The system does not need to be actively shaken, as is otherwise the case in a conventional shake culture. The cells remain alive in the scaffold. The influence of the system makes it possible to achieve considerably longer culturing times. Thus, the colonized system can be cultured for example over periods of several weeks, with the result that it can be used as a replacement product for animal testing. Culturing periods of several weeks were hitherto not possible for some cell types. Furthermore, the behavior of the cells can be tracked online since the system is preferably transparent to visible light. Continuous measurement using optical methods is ensured. In summary, the scaffold is novel in terms of its shape, architecture, method of use, and physical parameters.

These and other advantages and features of the invention will be apparent from the following description of representative embodiments, considered along with the accompanying drawings.

DESCRIPTION OF REPRESENTATIVE EMBODIMENTS

Figure 1:
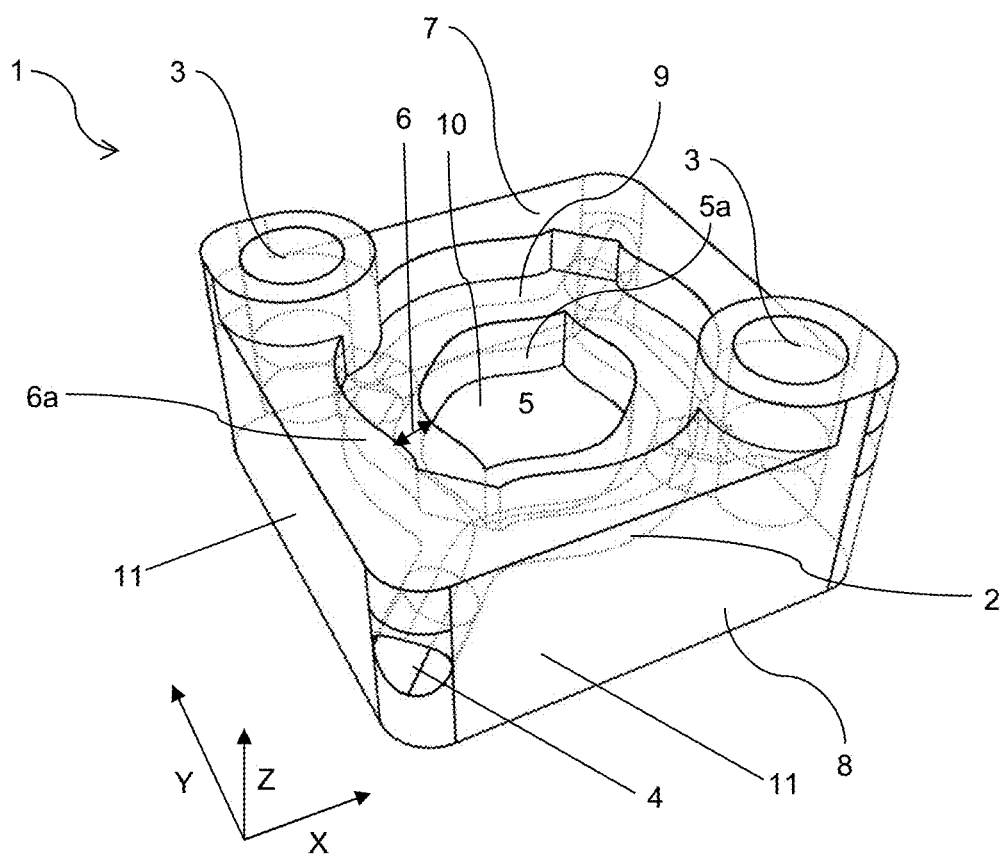
FIG. 1 shows a view of an uncolonized 3D scaffold of a CAD file with a central colonization chamber as well as two canal-type vessels surrounding the colonization chamber with two filling openings on the top side and two lateral outlet openings.

FIG. 1 shows a model of a 3D scaffold 1, created in a CAD file, which can be used according to the invention. The 3D scaffold 1 is preferably formed square with rounded corners. The 3D scaffold 1 preferably has a central recess which is open at the top as a colonization chamber 5 for biological cells. The entire outer perimeter of the recess which forms the colonization chamber 5 is defined by a recess lateral surface 5a. This recess lateral surface 5a extends continuously from a bottom surface of the recess shown at plane 10 in FIG. 1 along the entire dimension of the recess in the direction of the Z axis. Furthermore, 3D scaffold 1 preferably has a canal-type vessel 2 which is closed at the top and which preferably extends around the central colonization chamber 5 in the horizontal plane. The top side 7 of the 3D scaffold 1 preferably lies in the horizontal plane which is spanned by the X and Y axes. Likewise, the underside 8 preferably also lies in a horizontal plane which is also spanned by the X and Y axes. The top side 7 and the underside 8 are preferably substantially congruent. The height or depth of the 3D scaffold 1 extends in the direction of the Z axis. The colonization chamber 5 and the canal-type vessel 2 are preferably spatially separated from each other by a separation region 6 comprising a separation structure formed from biocompatible polymer. This separation structure has an inner surface comprised of at least a portion of the recess lateral surface 5a and an outer surface 6a facing the canal-type vessel 2. The recess which forms the colonization chamber 5 and is open towards the top side 7 is preferably arranged in the middle of the top side 7 with respect to the horizontal plane which is spanned by the X and Y axes and extends in a direction perpendicular to the horizontal plane, the Z axis, towards the underside 8 of the 3D scaffold 1. In the direction of the underside 8 the recess which forms the colonization chamber 5 is preferably capped off by biocompatible polymer, with the result that a cell suspension with which it has been filled cannot escape. At the side of the plane which is spanned by the X and Y axes, the recess is surrounded by an edge of the 3D scaffold. The colonization chamber 5 that is open towards the top side 7 is preferably formed annular with respect to its horizontal extent. The recess that is open towards the top side 7 is particularly preferably formed mirror-symmetrical with respect to its horizontal extent. In the plane which is spanned by the X and Y axes, the size of the extent of the recess preferably decreases in the direction of the Z axis towards the underside 8, particularly preferably in steps. The recess quite particularly preferably has a first plane 9 and a second plane 10, which are both spanned by the X and Y axes. The size of the extent of the first plane 9 is preferably greater than the size of the extent of the second plane 10 (both with respect to their extent in planes which are spanned by the X and Y axes), and preferably merge into each other with a step. The first plane 9 preferably lies closer to the top side 7 of the 3D scaffold than the second plane 10. Above the second plane 10 the colonization chamber 5 is preferably surrounded by the canal-type vessel 2, which preferably extends substantially along a plane which is spanned by the X and Y axes ("substantially" is to mean herein that the canal-type vessel 2 can have a slight downward slope in relation to the direction of the Z axis). Due to the spatial proximity of the colonization chamber 5 above the second plane 10, it can be supplied with nutrients from the canal-type vessel 2. Furthermore, it is preferred that the canal-type vessel 2 runs below the first plane 9, with the result that the colonization chamber 5 above the first plane 9 is also spatially adjacent and can be supplied with nutrients from the canal-type vessel 2. The canal-type vessel 2 preferably surrounds the colonization chamber 5 that is open towards the top side 7 annularly. The 3D scaffold 1 preferably has two filling openings 3 for the canal-type vessel 2, which are preferably arranged on the top side 7 of the 3D scaffold 1 in the form of filler necks. The two filling openings 3 in this case are preferably arranged on opposite sides, in particular at corners. This has the advantage that the canal-type vessel 2 running annularly around the colonization chamber 5 can be evenly supplied with a nutrient solution. The 3D scaffold 1 preferably has two outlet openings 4 for the canal-type vessel 2, which are preferably arranged on the lateral surfaces 11 of the 3D scaffold 1, here on the corner edges of the 3D scaffold 1, which run perpendicular to the plane of the top side 7. The two outlet openings 4 are preferably arranged at opposite corners of the 3D scaffold 1. The presence of two filling openings 3 and two outlet openings 4 of a canal-type vessel 2 that is formed annular makes it possible to supply the biological cells evenly with nutrients.

Figure 2:
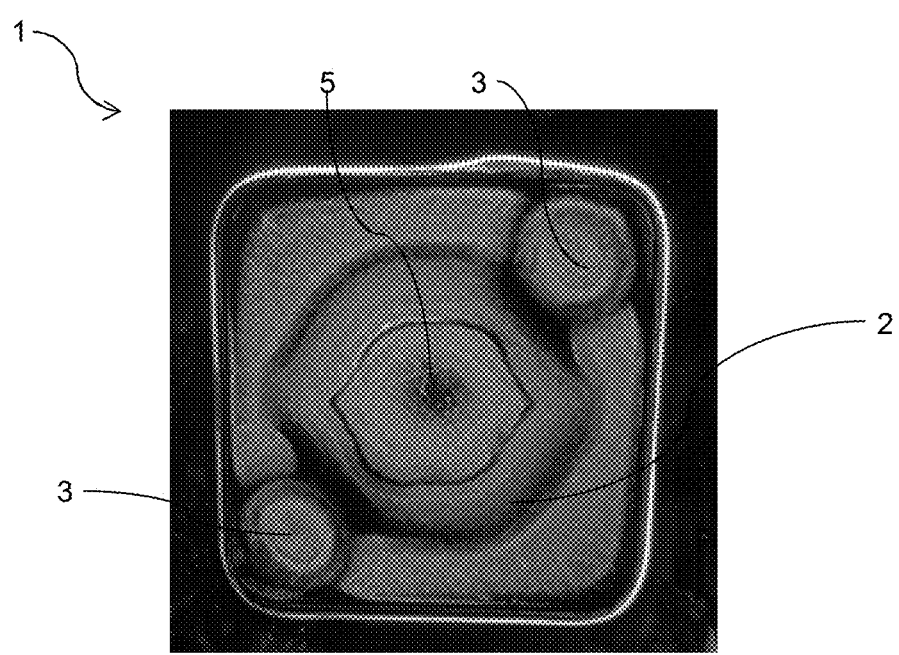
FIG. 2 shows a micrograph of a printed model according to the CAD file according to FIG. 1, from below.

FIG. 2 shows an actually printed 3D scaffold 1 under the microscope, from the underside thereof. Filler necks 3, canal-type vessels 2 and colonization chamber 5 can clearly be seen. The 3D scaffold shown in FIG. 2 is produced by the following method steps:

1.) creating the CAD file and calculating the master;
2.) equipping the printer with the photopolymerizable or photocrosslinkable liquids to be used;
3.) calibrating the printer, the axes and the printhead;
4.) carrying out the printing; the print platform lowers to the first printing plane for the first photopolymerizable or photocrosslinkable liquid;
5.) printing a first polymer from the first photopolymerizable or photocrosslinkable liquid for architectures consisting of polymer 1 for the first layer height of the construct to be printed; in the process, the calculated construction plan of the first polymer for the first layer height of the construct is projected onto the printing plane in which the printhead is located; here, one or more constructs can be produced simultaneously, depending on the user's wishes and plans; the limiting factor here is the size of the print platform or the installation space;
6.) if necessary, step of washing the printer in order to prevent the first polymer spreading into a second photopolymerizable or photocrosslinkable liquid and vice versa—optional (if a second polymer is required);
7.) if necessary, printing the second polymer for architectures consisting of the second polymer for the first layer—optional (if a second polymer is used);
8.) repeating steps six and seven if a third polymer is used;
9.) changing the printing plane in order to be able to print the second layer height;
10.) printing the first polymer for architectures consisting of the first polymer for the second layer height of the construct to be printed;
11.) if necessary, step of washing the printer in order to prevent the first polymer spreading into the second photopolymerizable or photocrosslinkable liquid and vice versa—optional (if a second polymer is used);
12.) if necessary, printing the second polymer from a second photopolymerizable or photocrosslinkable liquid for architectures consisting of the second polymer for the second layer—optional (if a second polymer is used);
13.) repeating steps 11 and 12 if a third polymer is required;
14.) changing the printing plane in order to be able to print the third layer height;
15.) repeating steps five to eight until the complete architecture has been printed;
16.) after completion of the printing, the print platform is moved into the starting plane and the 3D scaffold obtained is removed;
17.) subsequently, the 3D scaffold can be dried or used immediately;
18.) if the 3D scaffold is dried, this takes place in a sterile atmosphere; here, all water is removed from the 3D scaffold, with the result that a dry polymer scaffold is formed;
19.) after drying, the 3D scaffold can be stored under sterile conditions.

Specific conditions and parameters for the production of the 3D scaffold according to FIG. 2:
external diameter of 3D scaffold: 5.0 mm
height of 3D scaffold: 2.5 mm
volume of colonization chamber: 12 mm$^3$
internal diameter of filling openings: 1.2 mm
diameter of canal-type vessels
and outlet openings: 0.7 mm
composition of photocrosslinkable liquid:
  solvent: RPMI 1640+25 mM HEPES (Biochrom FG 1383), phosphate-buffered saline
  photocrosslinkable substance: gelatin methacrylate, 50 g/kg; polyethylene glycol diacrylate, 50 g/l
  further additives: lithium phenyl-2,4,6-trimethylbenzoylphosphinate, 5 g/kg; tartrazine, 2 mM;

In this example, the entire 3D scaffold is printed from the photocrosslinkable liquid. Adding the photoblocker tartrazine to the photocrosslinkable liquid regulates the penetration depth of the light used for the polymerization, enabling the production of the canal-type vessels. Alternatively, for producing the canal-type vessel, use could be made of sacrificial inks (used in a further photocrosslinkable liquid, e.g. 15 g/kg hyaluronic acid dissolved in RPMI+5 g/kg lithium phenyl-2,4,6-trimethylbenzoylphosphinate, printed and subsequently digested with hyaluronidase in order to produce the vessel), which are dissolved hydrolytically or by enzymatic digestion after completion of the printing.

Figure 3:
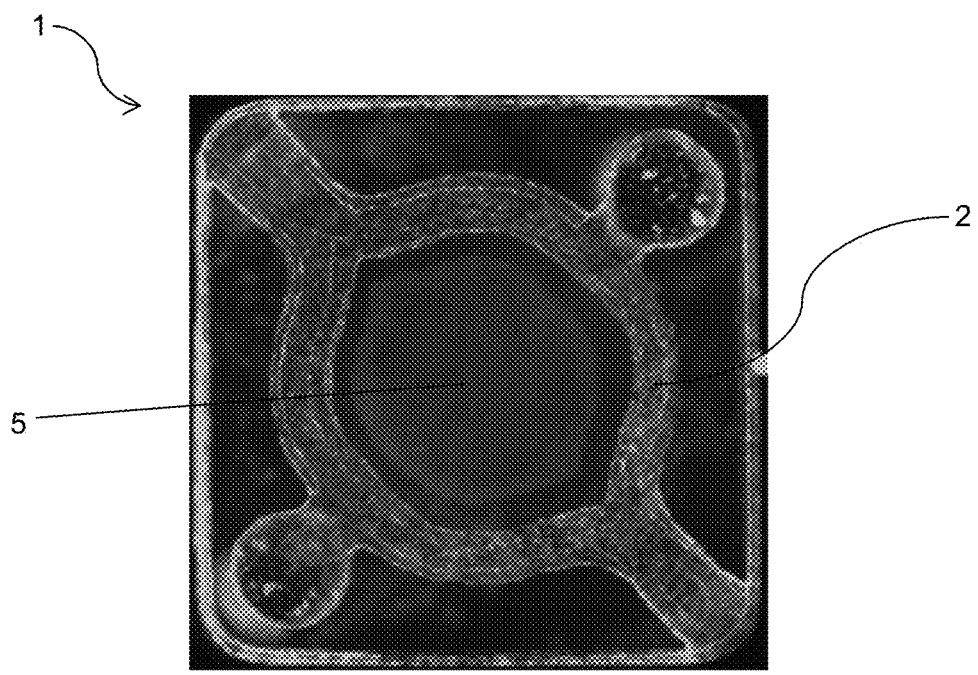
FIG. 3 shows a fluorescence micrograph of a 3D scaffold according to the invention according to FIG. 2, which selectively illustrates the vascular cells seeded in the canal-type vessel.
Figure 4:
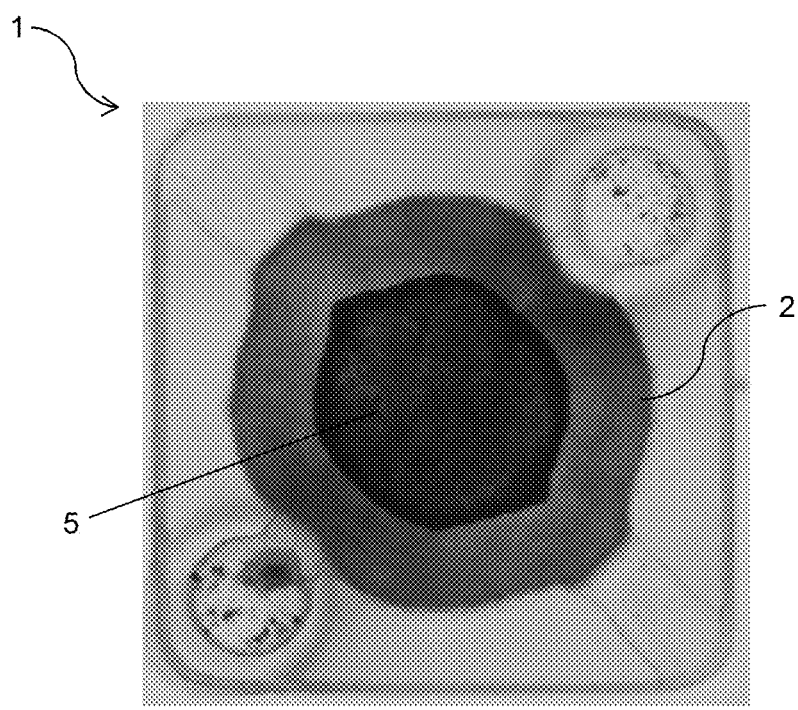
FIG. 4 shows a photograph in transmitted light of a 3D scaffold according to the invention according to FIG. 2, which shows a cell mass that has colonized in the central colonization chamber.

FIG. 3 shows a fluorescence micrograph and FIG. 4 a photograph in transmitted light of the canal-type vessel 2 colonized with human venous vascular cells of the umbilical cord and of the colonization chamber 5 colonized with human mesenchymal stromal cells. To this end, the following further method steps are carried out:

20.) a cell suspension having a concentration set beforehand by the user is pipetted into the colonization chamber of the 3D scaffold produced according to 1.) to 19.); in the process, a cell suspension volume is used which corresponds at most to the volume of the colonization chamber of the 3D scaffold; furthermore, a cell suspension having a concentration set beforehand by the user is pipetted via the two filler necks into the canal-type vessels; if the 3D scaffold is dried in step 18.), it must first be rehydrated by the user for reuse; a sterile medium such as water, PBS, cell culture medium or the like is suitable for this purpose;

21.) through the pipetting the suspensions are distributed within the 3D scaffold and the cells can be cultured within the 3D scaffold.

The colonizations are performed in a sterile Petri dish (diameter 10 cm), which is also utilized for the later culture of the 3D scaffold 1. The 3D scaffold 1 is placed, hydrated, in the empty Petri dish.

Human mesenchymal stromal cells (hMSC) are seeded into the central colonization chamber 5. For this, a cell suspension with 20 million hMSCs per milliliter is prepared in the culture medium DMEM high glucose +pyruvate +L-glutamine +10% fetal bovine serum +1% penicillin/streptomycin, and 10 l thereof is pipetted into the colonization region that has been drained beforehand.

The canal-type vessel 2 is colonized with human venous vascular cells from the umbilical cord (HUVECs). For this, a cell suspension with 50 million HUVECs per milliliter is prepared in the commercially available culture medium Endothelial Cell Growth Medium 2 (PromoCell GmbH) +1% penicillin/streptomycin, and 1.5 l thereof is in each case pipetted in per neck.

After the colonizations, the 3D scaffold 1 in the closed Petri dish is placed in an incubator to rest for 30 min (37° C., 5% $CO_2$). The co-culture medium Endothelial Cell Growth Medium 2 (PromoCell GmbH) +1% penicillin/streptomycin is then added and the submerged cell scaffold is cultured at 37° C. and in a 5% $CO_2$ atmosphere.

As used herein, whether in the above description or the following claims, the terms "comprising," "including," "carrying," "having," "containing," "involving," and the like are to be understood to be open-ended, that is, to mean including but not limited to.

The above-described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

LIST OF REFERENCE NUMBERS 1 3D scaffold
2 canal-type vessel
3 filling opening
4 outlet opening
5 colonization chamber
5a recess lateral surface
6 separation region
6a outer surface of separation structure
7 top side
8 underside
9 first plane
10 second plane
11 lateral surfaces

The invention claimed is:

1. A 3D scaffold comprising:
(a) a colonization chamber for biological cells, the colonization chamber comprising a recess that is open toward a top side of the 3D scaffold and extends along an X axis, a Y axis,
and a Z axis where the Y axis is orthogonal to and defines an X-Y plane with the X axis
and where the Z axis is orthogonal to both the X axis and the Y axis, the entire outer perimeter of the recess in planes parallel to the X-Y plane being defined by a recess lateral surface that extends continuously from a bottom surface of the recess along the entire dimension of the recess in the direction of the Z axis;
(b) a canal vessel in an interior of the 3D scaffold, the canal vessel at least partially surrounding the colonization chamber in planes parallel to the X-Y plane so as to be positioned between the colonization chamber and the periphery of the 3D scaffold in planes parallel to the X-Y plane;
(c) a filling opening for the canal vessel;
(d) an outlet opening for the canal vessel;
(e) wherein the 3D scaffold is comprised of biocompatible polymer; and
(f) wherein the colonization chamber and the canal vessel are spatially separated from each other in planes parallel to the X-Y plane by a separation structure, the separation structure having an inner surface comprised of at least a portion of the recess lateral surface and an outer surface facing the canal vessel, and the separation structure including a-separation structure biocompatible polymer that is permeable to nutrients in a direction from the canal vessel to the colonization chamber to facilitate diffusion of nutrients from the canal vessel into the colonization chamber.

2. The 3D scaffold of claim 1 wherein:
(a) the recess is located in a middle of the top side along a plane parallel to the X-Y plane; and
(b) the recess extends along the Z axis towards an underside of the 3D scaffold.

3. The 3D scaffold of claim 2 wherein the recess is formed annular, circular, oval, or in a mixed form with respect to the extent of the recess parallel to the X-Y plane.

4. The 3D scaffold of claim 2 wherein the extent of the recess parallel to the X-Y plane decreases in the direction of the Z axis from the top side of the 3D scaffold to the underside of the 3D scaffold.

5. The 3D scaffold of claim 2 wherein the extent of the recess parallel to the X-Y plane decreases in steps.

6. The 3D scaffold of claim 1 wherein the recess at a first point along the Z axis has a first extent parallel to the X-Y plane and at a second point along the Z axis has a second extent parallel to the X-Y plane, the first extent being greater than the second extent.

7. The 3D scaffold of claim 1 wherein the canal vessel surrounds the recess annularly along a plane parallel to the X-Y plane.

8. The 3D scaffold of claim 1 further including an additional filling opening for canal vessel and wherein the filling opening and the additional filling opening are arranged on the top side of the 3D scaffold.

9. The 3D scaffold of claim 1 further including an additional outlet opening for the canal vessel and wherein the outlet opening and the additional outlet opening are arranged on lateral surfaces of the 3D scaffold which run perpendicular to a plane of the top side of the 3D scaffold.

10. The 3D scaffold of claim 1 produced by a lithographic 3D printing method.

11. The 3D scaffold of claim 1 wherein the colonization chamber is colonized with biological cells.

12. The 3D scaffold of claim 1 wherein the permeability of the separation structure biocompatible polymer to facilitate diffusion of nutrients from the canal vessel into the colonization chamber is defined by interstices between polymer molecules making up the separation structure biocompatible polymer.

13. The 3D scaffold of claim 12 wherein the permeability of the separation structure biocompatible polymer to facilitate diffusion of nutrients from the canal vessel into the colonization chamber is defined in part by a degree of crosslinking between crosslinkable units in the separation structure biocompatible polymer.

14. A method of using the 3D scaffold according to claim 1 including colonizing the colonization chamber with biological cells and supplying the biological cells with nutrients within the 3D scaffold.

* * * * *